US011337859B2

(12) United States Patent
Young

(10) Patent No.: US 11,337,859 B2
(45) Date of Patent: May 24, 2022

(54) GOGGLE MUD SHIELD

(71) Applicant: 100% Speedlab, LLC, San Diego, CA (US)

(72) Inventor: Michael D. Young, San Diego, CA (US)

(73) Assignee: 100% Speedlab, LLC, San Diego, CA (US)

( * ) Notice: Subject to any disclaimer, the term of this patent is extended or adjusted under 35 U.S.C. 154(b) by 0 days.

(21) Appl. No.: 16/942,665

(22) Filed: Jul. 29, 2020

(65) Prior Publication Data

US 2021/0030592 A1 Feb. 4, 2021

Related U.S. Application Data

(60) Provisional application No. 62/879,939, filed on Jul. 29, 2019.

(51) Int. Cl.
*A61F 9/02* (2006.01)
(52) U.S. Cl.
CPC .............. *A61F 9/025* (2013.01); *A61F 9/029* (2013.01)
(58) Field of Classification Search
CPC .......... A61F 9/025; A61F 9/029; A61F 9/022; A61F 9/02; A61F 9/023; A61F 9/024; A42B 3/26
USPC ..... 2/431, 426, 422, 438; 128/201.14; 351/4
See application file for complete search history.

(56) References Cited

U.S. PATENT DOCUMENTS

| 3,702,607 | A | | 11/1972 | Johnson et al. |
| 3,945,044 | A | | 3/1976 | Mcgee et al. |
| 3,946,442 | A | | 3/1976 | Wallander |
| 4,076,373 | A | | 2/1978 | Moretti |
| 4,428,081 | A | | 1/1984 | Smith |
| 4,528,701 | A | * | 7/1985 | Smith ........................ A61F 9/02 2/438 |
| 4,542,538 | A | * | 9/1985 | Moretti ................ A62B 18/082 2/205 |
| 4,748,697 | A | | 6/1988 | Hodnett |
| 4,755,040 | A | | 7/1988 | Haslbeck |
| 5,163,185 | A | | 11/1992 | Hodnett |
| 5,203,035 | A | * | 4/1993 | Lawlor ................... A61F 9/025 2/434 |
| 5,546,611 | A | | 8/1996 | Lathrop |
| 5,913,416 | A | | 6/1999 | Rothan |

(Continued)

FOREIGN PATENT DOCUMENTS

| GB | 2378412 A | 2/2003 |
| GB | 2495984 A | 5/2013 |

OTHER PUBLICATIONS

Korean Intellectual Property Office, International Search Report and Written Opinion of the International Searching Authority, dated Nov. 13, 2020, in PCT/US2020/044116 which is the international application which shares the same priority as this U.S. application.

*Primary Examiner* — F Griffin Hall
(74) *Attorney, Agent, or Firm* — Kolitch Romano LLP

(57) ABSTRACT

A mud shield configured to attach to a goggle frame or an adaptor to a goggle frame is disclosed. The mud shield may include a shield body configured to be disposed over at least a portion of a goggle. The mud shield may be configured such that mud, water, or other debris may roll off of the mud shield over the front of the film, preventing the mud, water, or other debris from being smeared between a goggle lens and a film disposed on the goggle lens.

18 Claims, 12 Drawing Sheets

(56) References Cited

U.S. PATENT DOCUMENTS

| | | | |
|---|---|---|---|
| 5,966,745 A | 10/1999 | Schwartz et al. | |
| 6,065,833 A * | 5/2000 | Tiano | A61F 9/029 2/435 |
| 6,206,521 B1 | 3/2001 | Kindschuh | |
| 6,415,452 B1 | 7/2002 | Watanabe | |
| 6,416,177 B1 | 7/2002 | Gibson | |
| 7,866,812 B1 | 1/2011 | Tullis | |
| 8,356,895 B2 | 1/2013 | Jackson et al. | |
| 8,782,820 B2 | 7/2014 | Park | |
| 9,839,558 B2 | 12/2017 | Blanchard et al. | |
| 10,123,907 B2 | 11/2018 | Sigismondo et al. | |
| 2001/0029623 A1 | 10/2001 | Tsubooka | |
| 2002/0166158 A1 | 11/2002 | Chiang | |
| 2003/0099474 A1 | 5/2003 | Takatori | |
| 2009/0119823 A1 | 5/2009 | Lee | |
| 2009/0229044 A1 | 9/2009 | Gill | |
| 2010/0033671 A1 | 2/2010 | Campo | |
| 2011/0069274 A1 | 3/2011 | Han et al. | |
| 2012/0023647 A1 | 2/2012 | Park | |
| 2013/0104299 A1 | 5/2013 | Chen | |
| 2014/0157496 A1 | 6/2014 | Ginther et al. | |
| 2014/0196199 A1 * | 7/2014 | Huffman | A42B 3/20 2/421 |
| 2015/0067952 A1 | 3/2015 | Kulik | |
| 2015/0320600 A1 | 11/2015 | Blanchard et al. | |
| 2015/0328050 A1 | 11/2015 | Sigismondo et al. | |
| 2016/0054582 A1 | 2/2016 | Rauter | |
| 2017/0100286 A1 | 4/2017 | Salmini et al. | |

\* cited by examiner

GOGGLE MUD SHIELD

CROSS-REFERENCES

The following applications and materials are incorporated herein, in their entireties, for all purposes: U.S. Provisional Patent Application Ser. No. 62/879,939, filed Jul. 29, 2019.

FIELD

This disclosure relates to systems and methods for goggle mud and debris management systems. More specifically, the disclosed embodiments relate to sport goggles and to a mud shield for use with sport goggles.

INTRODUCTION

Sport goggles are worn by users for various sports or activities, such as motorsports, powersports, snowsports, watersports, biking, and the like, to protect the face and eyes. Roll-off film systems have been developed for sport goggles to preserve a field of view on the lens of the sport goggle. In particular, the roll-off film system may stretch a section of a clear film across the lens of the sport goggle. When the section of the clear film is filled with dirt or debris from the sport activity, the roll-off film system may convey the used section of the clear film off the lens and a new section of the film may be conveyed onto the lens to provide a clear field of view for the user.

Nevertheless, dirt or mud may enter through an interface between the roll-off film system and the lens of the goggle. This can reduce the field of view on the lens, rendering the roll-off film system ineffective. As such, there is a need for an improved implementation that may address one or more of these shortcomings.

SUMMARY

The present disclosure provides systems, apparatuses, and methods relating to improved mud shields for use with goggles.

In some embodiments, a mud shield may include a shield body configured to be disposed over at least a portion of a goggle. The shield body may include a shield top portion, a shield bottom portion, and an opening. The shield top portion may be configured to be disposed over an upper portion of the goggle and include a top edge. The shield bottom portion may be configured to be disposed over a lower portion of the goggle and include a bottom edge. The opening may be defined, at least in part, by the top edge and the bottom edge. The top edge may be configured to be disposed over a film area of a lens of the goggle.

In some embodiments, the top edge may include a top seal edge configured to contact a top portion of a film of the lens. In a certain embodiment, the shield top portion may be configured to fully cover a top portion of the lens of the goggle above the film area. In a certain embodiment, the bottom edge may include a bottom seal edge configured to a contact a bottom portion of a film of the lens. In a certain embodiment, the mud shield may further include a left portion that includes a left edge and a right portion that includes a right edge. The opening may be substantially rectangular in shape and is further defined, at least in part, by the left edge and the right edge. In a certain such embodiment, the left edge may include a left seal edge, the right edge may include a right seal edge, and at least portions of the left seal edge and the right seal edge are configured to be disposed on the film. In a further such embodiment, the left portion and the right portion are configured to cover at least a portion of a left cannister and a right cannister, respectively.

In some embodiments, the shield bottom portion may include one or more forms on a rear side of the shield bottom portion. In a certain such embodiment, the forms are configured to dispose at least a portion of the bottom edge away from the film.

In some embodiments, the mud shield may further include a tab configured couple the shield body to the goggle. In a certain embodiment, the mud shield may further include a pin opening configured to allow a pin of the goggle or a canister to pass through.

In some embodiments, a method of using the mud shield may be disclosed. The method may include coupling the mud shield to the goggle and preventing or minimizing debris from flowing into the upper portion of the goggle with the shield top portion. In some embodiments, a goggle system may include a goggle and a mud shield.

The goggle may include a goggle frame and a lens coupled to the goggle frame and including a film area configured to receive a film. The mud shield may include a shield body configured to be disposed over at least a portion of the goggle. The shield body may include a shield top portion configured to be disposed over an upper portion of the goggle and including a top edge, a shield bottom portion configured to be disposed over a lower portion of the goggle and including a bottom edge, and an opening defined, at least in part, by the top edge and the bottom edge, the top edge being configured to be disposed over the film area.

In some embodiments, the goggle system may further include the film, where the film is conveyed across the lens. In a certain such embodiment, the top edge may include a top seal edge configured to contact a top portion of the film. In a further such embodiment, the goggle system may further include a left canister and a right canister, where the film is conveyed from one of the left canister or the right canister to the other of the left canister or the right canister.

In some embodiments, the shield top portion may be configured to fully cover a top portion of the lens of the goggle above the film area. In a certain embodiment, the bottom edge may include a bottom seal edge configured to a contact a bottom portion of the film. In a certain embodiment, the mud shield may further include a left portion including a left edge and a right portion including a right edge, where the opening is substantially rectangular in shape and is further defined, at least in part, by the left edge and the right edge. In a certain such embodiment, the left edge may include a left seal edge, the right edge may include a right seal edge, and at least portions of the left seal edge and the right seal edge are configured to be disposed on the film.

Features, functions, and advantages may be achieved independently in various embodiments of the present disclosure, or may be combined in yet other embodiments, further details of which can be seen with reference to the following description and drawings.

DETAILED DESCRIPTION

Figure 1:
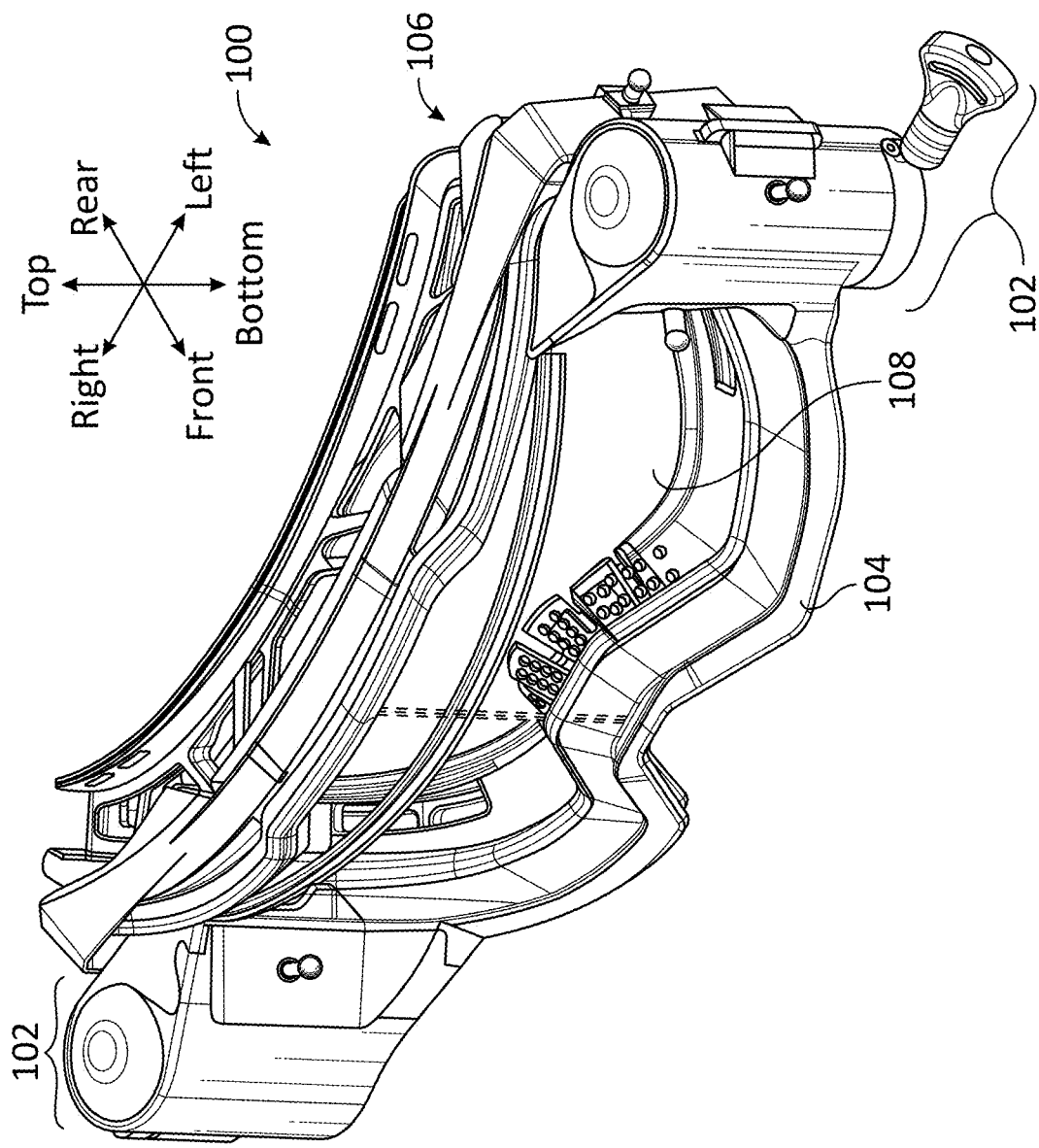
FIG. 1 is a perspective front view of an illustrative roll-off film system installed on a goggle, in accordance with aspects of the present disclosure.

Various aspects and examples of a mud shield configured to attach to a goggle frame or an adaptor to a goggle frame, as well as related methods, are described below and illustrated in the associated drawings. Unless otherwise specified, a mud shield in accordance with the present teachings, and/or its various components, may contain at least one of the structures, components, functionalities, and/or variations described, illustrated, and/or incorporated herein. Furthermore, unless specifically excluded, the process steps, structures, components, functionalities, and/or variations described, illustrated, and/or incorporated herein in connection with the present teachings may be included in other similar devices and methods, including being interchangeable between disclosed embodiments. The following description of various examples is merely illustrative in nature and is in no way intended to limit the disclosure, its application, or uses. Additionally, the advantages provided by the examples and embodiments described below are illustrative in nature and not all examples and embodiments provide the same advantages or the same degree of advantages.

This Detailed Description includes the following sections, which follow immediately below: (1) Definitions; (2) Overview; (3) Examples, Components, and Alternatives; (4) Advantages, Features, and Benefits; and (5) Conclusion. The Examples, Components, and Alternatives section is further divided into subsections A through E, each of which is labeled accordingly.

Definitions

The following definitions apply herein, unless otherwise indicated.

"Comprising," "including," and "having" (and conjugations thereof) are used interchangeably to mean including but not necessarily limited to, and are open-ended terms not intended to exclude additional, unrecited elements or method steps.

Terms such as "first", "second", and "third" are used to distinguish or identify various members of a group, or the like, and are not intended to show serial or numerical limitation.

"AKA" means "also known as," and may be used to indicate an alternative or corresponding term for a given element or elements.

"Elongate" or "elongated" refers to an object or aperture that has a length greater than its own width, although the width need not be uniform. For example, an elongate slot may be elliptical or stadium-shaped, and an elongate candlestick may have a height greater than its tapering diameter. As a negative example, a circular aperture would not be considered an elongate aperture.

"Coupled" means connected, either permanently or releasably, whether directly or indirectly through intervening components.

"Resilient" describes a material or structure configured to respond to normal operating loads (e.g., when compressed) by deforming elastically and returning to an original shape or position when unloaded.

"Rigid" describes a material or structure configured to be stiff, non-deformable, or substantially lacking in flexibility under normal operating conditions.

"Elastic" describes a material or structure configured to spontaneously resume its former shape after being stretched or expanded.

"Providing," in the context of a method, may include receiving, obtaining, purchasing, manufacturing, generating, processing, preprocessing, and/or the like, such that the object or material provided is in a state and configuration for other steps to be carried out.

In this disclosure, one or more publications, patents, and/or patent applications may be incorporated by reference. However, such material is only incorporated to the extent that no conflict exists between the incorporated material and the statements and drawings set forth herein. In the event of any such conflict, including any conflict in terminology, the present disclosure is controlling.

Overview

In general, mud shields of the present disclosure include a shield body configured to be clipped onto or otherwise coupled to a goggle (e.g., to the goggle frame and/or an adaptor). The mud shield secures and seals an underlying film selectively passed across the lens of the goggle, such that the film and goggle lens are more effective as a system.

In some examples, the shield body is integrated into the goggle lens and/or frame. When in use, the mud shield is disposed over at least a portion of the goggle (e.g., a front portion). The shield body includes a shield top portion, a shield bottom portion, and an opening or gap formed between the top and bottom portions. The shield top portion is configured to be disposed over an upper portion of the goggle, and includes a first (lower) edge corresponding to a top edge of the opening or gap. The shield bottom portion is configured to be disposed over a lower portion of the goggle, and includes a second (upper) edge corresponding to a bottom edge of the opening or gap. The opening is defined, at least in part, by the top edge and the bottom edge. The top edge of the opening or gap is configured to be disposed over a film area of the lens of the goggle. The opening or gap defines a window in the mud shield, where a user's vision is unobstructed by the mud shield.

Mud shields of the present disclosure are configured to be used with a corresponding roll-off film system, although the roll-off film system is not required for the mud shield to be utilized. The roll-off film system includes a film dispensing canister configured to dispense a film (e.g., a visually transparent plastic film) across the goggle lens to a film receiving canister. In some known systems, a film is disposed on the goggle lens in a manner that allows mud, water, and other debris to work its way between the film and the lens, thereby clouding a user's vision. Mud shields of the present disclosure prevent debris from working in between the film and the goggle lens, and/or minimize an amount of debris that does work its way between the film and the goggle lens. The top edge of the mud shield opening includes a sealing feature (AKA a top seal edge) configured to overlap and contact a top outward-facing portion of the film. Accordingly, the mud shield is configured such that mud, water, and/or debris rolls off the shield top portion over the front of the film, preventing smearing between the film and the goggle lens. In some examples, the goggle includes a sealing feature at the bottom edge of the opening (AKA a bottom seal edge) configured to overlap and contact a bottom outward-facing portion of the film.

In some examples, the film is selectively conveyed laterally across the front of the lens (e.g., sliding across the lens between the lens and the mud shield). The lens of the goggle may include suitable feature(s) configured to facilitate sliding of the film across the lens (e.g., by inhibiting static cling, reducing friction, and/or the like). For example, one or more cords may be disposed on the lens of the goggle in a film area where the film slides across. The cords may be thin and/or at least partially transparent, so as not to inhibit the vision of a wearer of the goggle.) The film may be a roll of film dispensed from one canister and received by the other, the roll comprising a length of film longer than the length of the front of the lens. This allows a user of the system to dispense fresh film to replace used (e.g., dirty) film. In some examples, the film is dispensed from the canister in an indexed manner.

One or both lateral sides of the opening of the mud shield may include one or more sealing features. The seals on the lateral sides of the opening may contact the film and prevent mud, water, and/or debris from being pulled by the film into the canister.

EXAMPLES, COMPONENTS, AND ALTERNATIVES

The following sections describe selected aspects of illustrative mud shields, as well as related systems and/or methods. The examples in these sections are intended for illustration and should not be interpreted as limiting the scope of the present disclosure. Each section may include one or more distinct embodiments or examples, and/or contextual or related information, function, and/or structure.

A. Illustrative Goggle and Roll-Off Film System

Figure 2:
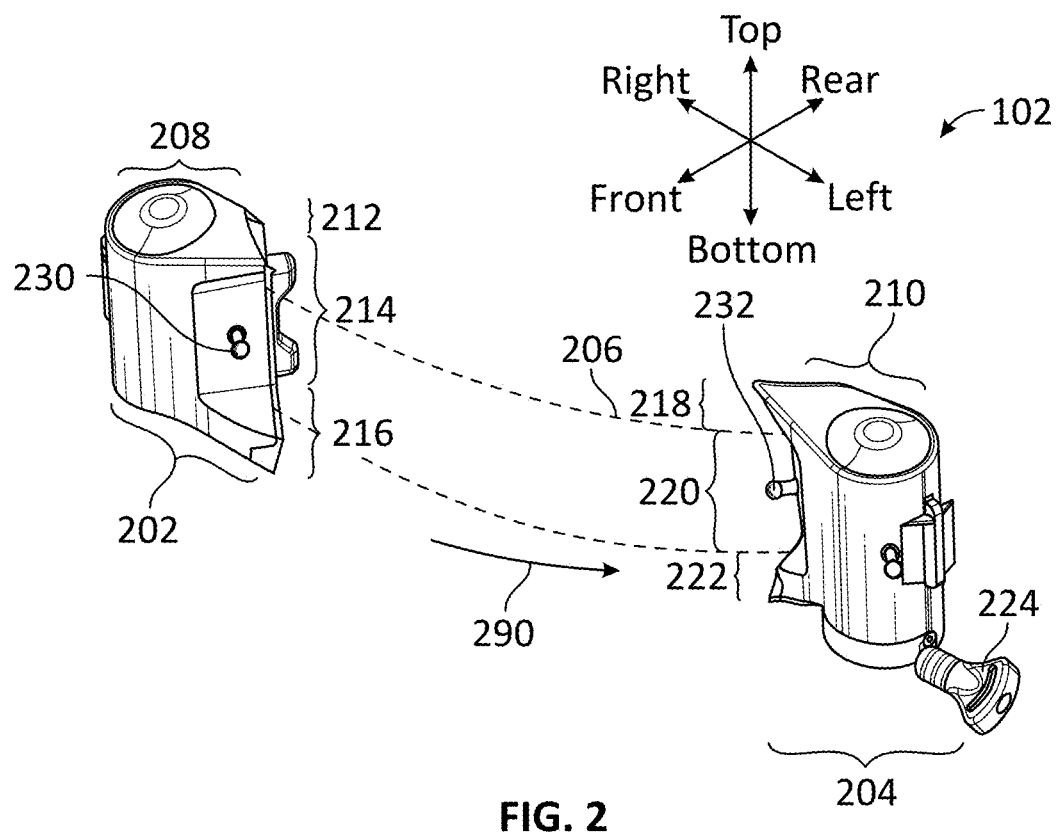
FIG. 2 is a perspective front view of the roll-off film system of FIG. 1.
Figure 3:
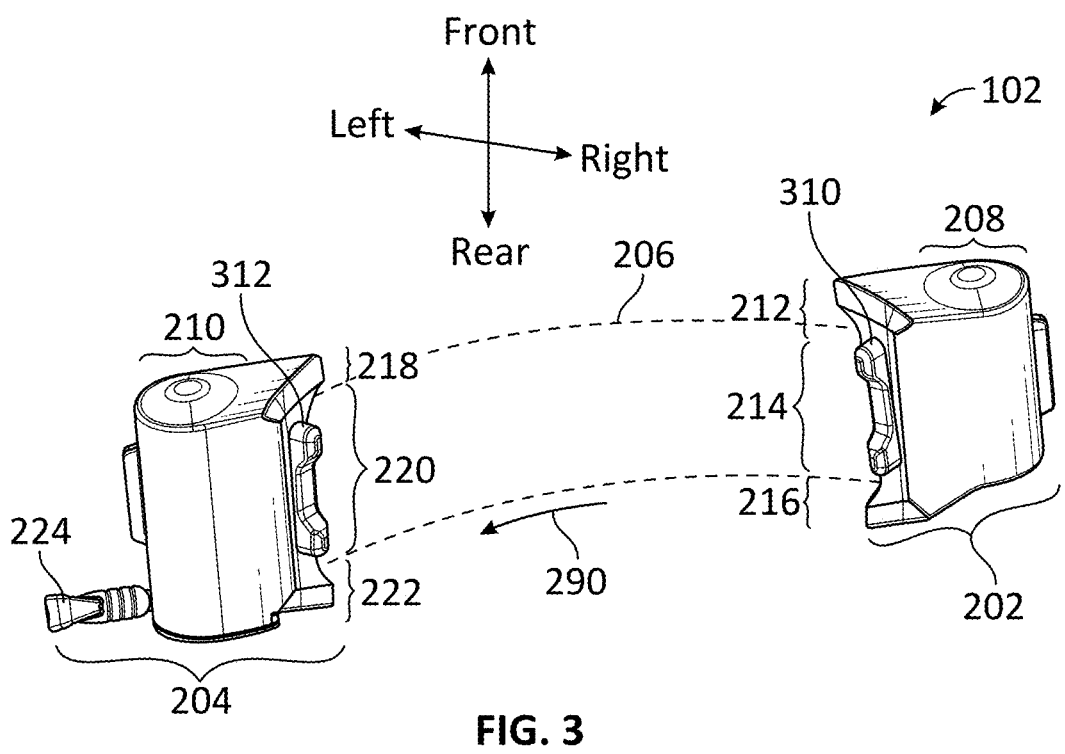
FIG. 3 is a perspective rear view of the roll-off film system of FIG. 1.

As shown in FIGS. 1-3, this section describes illustrative goggles and roll-off film systems suitable for use with mud shields of the present disclosure.

FIG. 1 is a perspective front view of an illustrative roll-off film system 102 installed on a goggle 100. As shown in FIG. 1, goggle 100 includes a goggle frame 106. In the depicted example, roll-off film system 102 is installed on (e.g., coupled to) goggle frame 106. Roll-off film system 102 is coupled to a front frame portion 104 of goggle frame 106. Roll-off film system 102 is configured to stretch a section of film on a lens 108 of the goggle. When the section of film becomes filled with dirt or debris, or otherwise obstructs or limits the extent of a user's field of view through lens 108, the used section of film may be conveyed off lens 108 and a new section of film may replace the used section to provide the user with clear field of view on or through lens 108.

FIGS. 2 and 3 show perspective front and rear views of roll-off film system 102 of FIG. 1. As shown in FIGS. 2 and 3, roll-off film system 102 includes a film dispensing canister 202 and a film receiving canister 204. Film dispensing canister 202, which may be referred to as a first or right canister, may dispense a section of a film 206 across lens 108 toward film receiving canister 204. Film receiving canister 204, which may be referred to as a second or left canister, receives film 206 from film dispensing canister 202. Film receiving canister 204 includes a pull cord handle 224, which is attached to an end of a string configured to drive a conveyance of film 206 from film dispensing canister 202 to film receiving canister 204 in a film conveying direction 290. For example, when the section of film 206 resting on lens 108 is desired to be removed from lens 108, such as after becoming covered with dirt or debris, a user pulls pull cord handle 224 to roll the used section of film 206 into film receiving canister 204 and to convey a new section of film 206 onto lens 108 to provide clear field of view on lens 108.

Film dispensing canister 202 includes a film storage portion 208 within which film 206 may be stored. Film dispensing canister 202 includes an upper wing portion 212, a lower wing portion 216, and a blade portion 214 disposed between upper wing portion 212 and lower wing portion 216. Each of upper wing portion 212, lower wing portion 216, and blade portion 214 extend away from film storage portion 208 toward film receiving canister 204. Upper wing portion 212 and lower wing portion 216 protrude further downstream in film conveying direction 290 than blade portion 214. Film 206 exits film dispensing canister 202 through an opening at or near blade portion 214. Film dispensing canister 202 includes a pin 230 extending from blade portion 214. Pin 230 may facilitate connection of various elements or accessories to film dispensing canister 202.

Film receiving canister 204 includes a film storage portion 210 within which film 206 received from the film dispensing canister 202 may be stored. Film receiving canister 204 also includes an upper wing portion 218, a lower wing portion 222 and, a blade portion 220 disposed between upper wing portion 218 and lower wing portion 222. Each of upper wing portion 218, lower wing portion 222, and blade portion 220 extend away from film storage portion 210 toward film dispensing canister 202. Upper wing portion 218 and lower wing portion 222 protrude further upstream in film conveying direction 290 than blade portion 220. Film 206 is conveyed into film receiving canister 204 through an opening at or near blade portion 220. Film receiving canister 204 includes a pin 232 extending from blade portion 220. Pin 232 facilitates connection of various elements or accessories to film receiving canister 204.

As shown in FIG. 3, film dispensing canister 202 includes a lens attachment mechanism 310 configured to attach film dispensing canister 202 to lens 108 or any other portion of goggle 100, such as to goggle frame 106. Similarly, film receiving canister 204 includes a lens attachment mechanism 312 configured to attach film receiving canister 204 to lens 108 or any other portion of goggle 100, such as to goggle frame 106. For instance, lens attachment mechanisms 310, 312 may couple to corresponding retention features defined in or coupled to lens 108, though other configurations are contemplated. Lens attachment mechanisms 310, 312 may be configured to releasably attach roll-off system 102 to lens 108. In this manner, roll-off system 102 and/or lens 108 may be replaced should roll-off system 102 or lens 108 become damaged. In some examples, roll-off system 102 is integrated with lens 108 such that roll-off system 102 and lens 108 are provided as a single assembly.

B. First and Second Illustrative Mud Shields

As shown in FIGS. 4A-9B, this section describes illustrative mud shields. These mud shields are examples of the mud shields described in the Overview above.

Figure 4A:
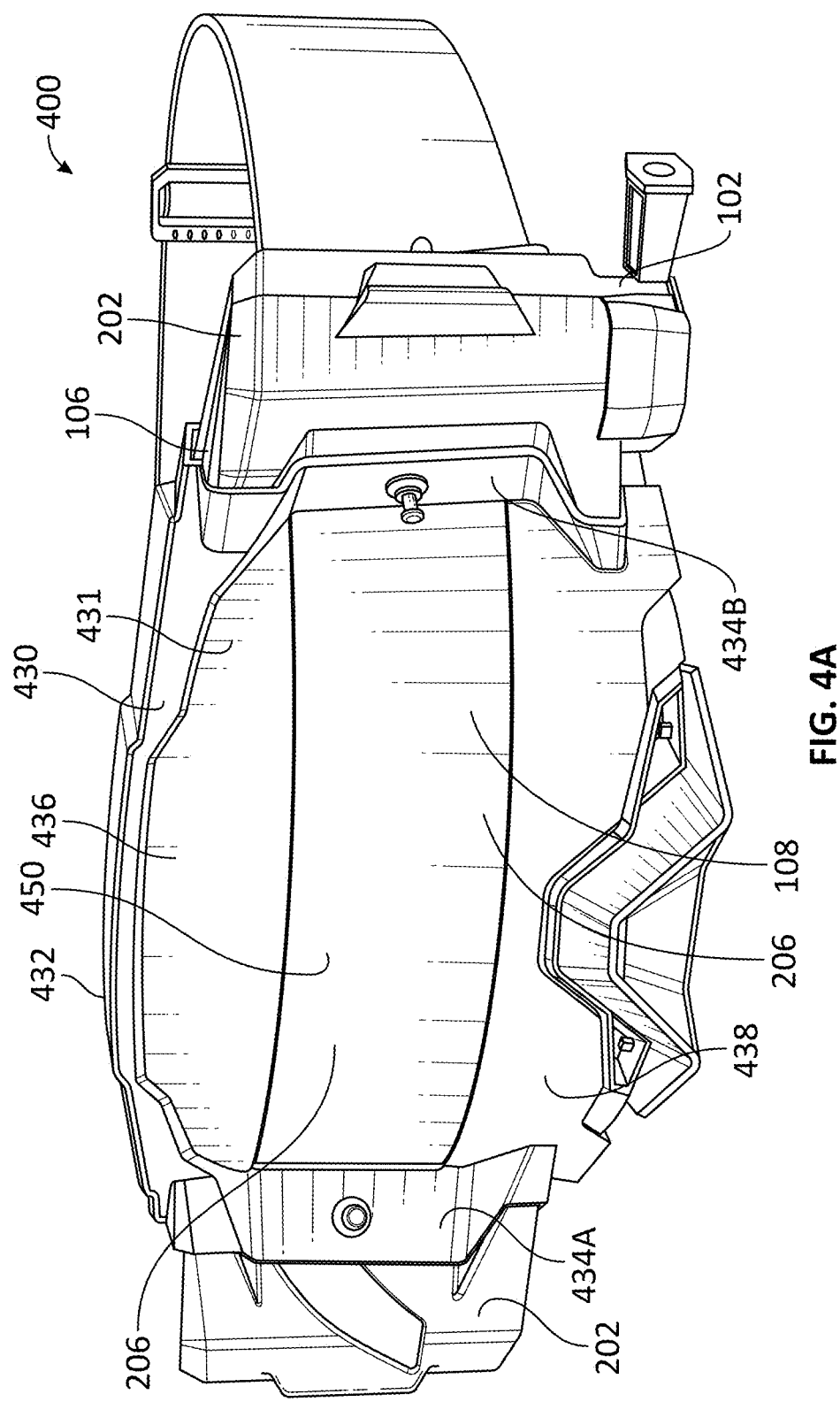
FIG. 4A is a perspective front view of a goggle having a first illustrative mud shield installed thereon, in accordance with aspects of the present disclosure.
Figure 4B:
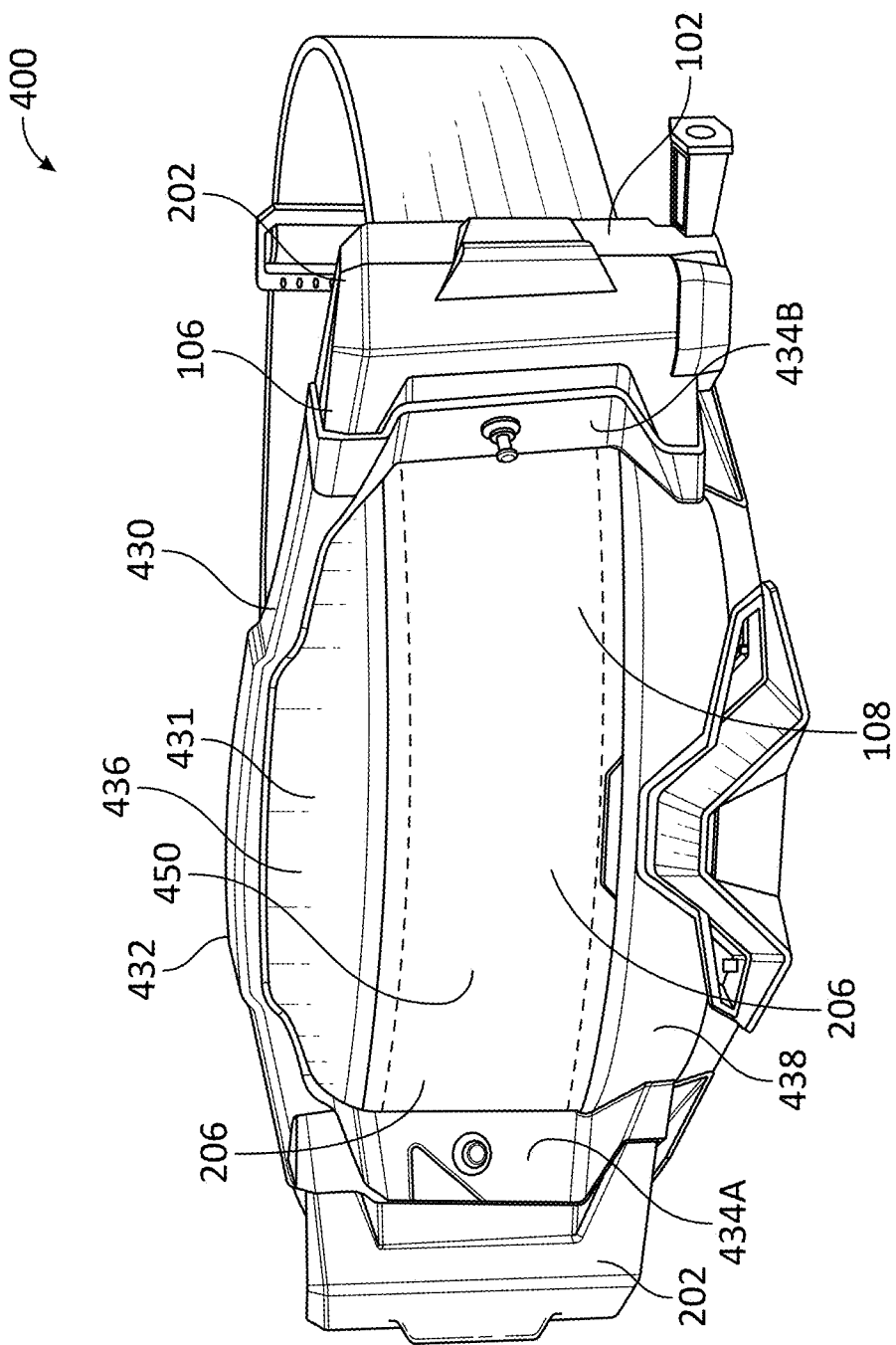
FIG. 4B is a perspective view of the goggle having a second illustrative mud shield installed thereon, in accordance with aspects of the present disclosure.

FIGS. 4A and 4B depict an illustrative goggle 400 that includes respective variations of a mud shield 430 mounted to and disposed over portions of goggle frame 106, lens 108, and/or roll-off film system 102. Goggle 400 is substantially similar to goggle 100 of FIG. 1, described above. In the examples of FIGS. 4A and 4B, mud shield 430 includes a shield body 431 configured to be disposed over at least a portion of goggle 400. In some examples, mud shield 430 includes a shield top portion 432 (including a shield lens top portion 436), a right portion 434A, a left portion 434B, and a shield bottom portion 438. Shield top portion 432, right portion 434A, left portion 434B, and shield bottom portion 438 define edges of an opening 450 (AKA a gap or window) within mud shield 430.

In some examples, the edges of opening 450 define the extent of a field of view through mud shield 430, such as when shield top portion 432, right portion 434A, left portion 434B, and shield bottom portion 438 comprise an opaque or semitransparent material. In some examples, the edges of opening 450 correspond to the section of film 206 resting on lens 108. For example, the top and bottom edges of opening 450, defined by shield top portion 432 and shield bottom portion 438, extend adjacent to upper and lower edges of film 206 when the film extends across lens 108. The edges of opening 450 defined by right portion 434A and left portion 434B, which may be referred to as right and left edges, respectively, extend adjacent to film dispensing canister 202 and film receiving canister 204, respectively, e.g., adjacent to blade portions 214 and 220.

Mud shield 430 may be molded, vacuumed formed, and/or otherwise manufactured from rubber, plastic(s), composite material(s), and/or any other appropriate material. All or portions of mud shield 430 may be transparent, translucent, opaque, and/or otherwise configured to allow and/or block any suitable amount and/or type of light. In some examples, mud shield 430 (and/or portions thereof) is clear, colored, or tinted as appropriate.

Portions of mud shield 430 are disposed over portions of goggle frame 106, lens 108, and/or roll-off film system 102. Mud shield 430 may be disposed over goggle frame 106 in a manner that prevents or reduces the amount of debris, such as mud, water, ice, snow, dirt, dust, and/or other such debris, from intruding into an area between film 206 and lens 108, as well as, in certain examples, from being pulled into film dispensing canister 202 and/or film receiving canister 204 by film 206. Thus, mud shield 430 may, as viewed from the top, front, or side, cover or prevent gaps between film 206 and lens 108 and between film 206 and an entry area of one or both of canisters 202.

For example, as shown in FIG. 4A and explained in further detail below, portions of mud shield 430 may extend or clip over portions of goggle frame 106. As shown in FIG. 4B and explained in further detail below, portions of mud shield 430 may extend or clip over portions of roll-off system 102. In some examples, mud shield 430 couples to film dispensing canister 202 and film receiving canister 204 of roll-off system 102. For example, right portion 434A and left portion 434B of mud shield 430 may couple with pins 230, 232 extending from canisters 202, 204. In some examples, pins 230, 232 are integrated with the mud shield, and mud shield 430 clips onto a back side of the canisters using one or more tabs and/or clips.

Figure 5A:
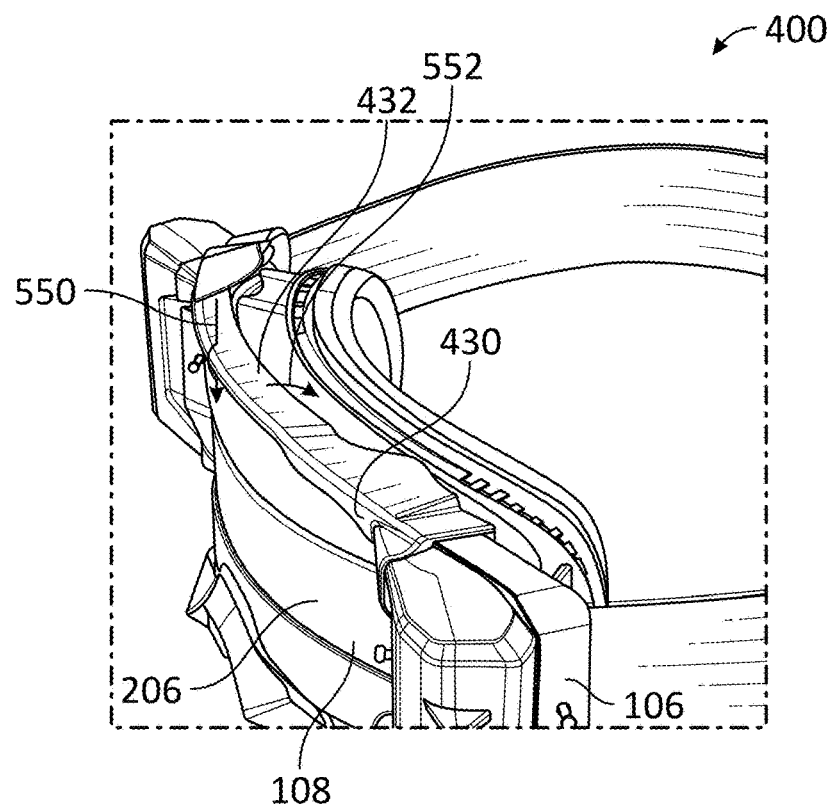
FIG. 5A is a perspective top view of a portion of the goggle with the installed mud shield of FIG. 4A.
Figure 5B:
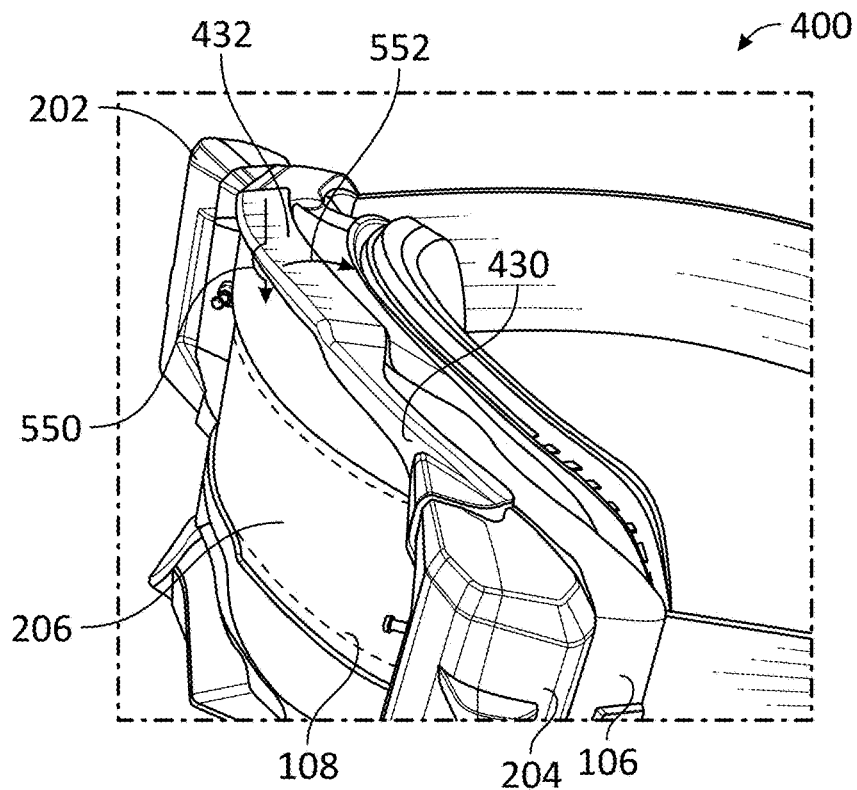
FIG. 5B is a perspective top view of a portion of the goggle with the installed mud shield of FIG. 4B.

FIG. 5A is a perspective top view of a portion of goggle 400 with the installed mud shield 430 of FIG. 4A. FIG. 5B is a perspective top view of a portion of goggle 400 with the installed mud shield 430 of FIG. 4B. As shown in FIG. 5A and explained in further detail below, portions of shield top portion 432 may extend or clip over portions of goggle frame 106. As shown in FIG. 5B and explained in further detail below, portions of shield top portion 432 may extend or clip over portions of roll-off system 102.

Shield top portion 432 includes shield lens top portion 436 that covers a top portion of lens 108 and overhangs the top of film 206 or an area of lens 108 where film 206 would be disposed. Shield top portion 432 may cover substantially (e.g., 70% or more, 80% or more, or 90% or more) all of the top portion of goggle 400 (as illustrated in FIGS. 5A and 5B) or lens 108 of goggle 400 above film 206, or may cover only a portion thereof. As shown in FIGS. 5A and 5B, debris that falls or flows off the front of shield top portion 432 flows in direction 550. Debris flowing in direction 550 flows down the front of shield top portion 432 over the front of film 206 instead of to the rear of film 206 (which may cloud the vision of the user in a manner that is hard to clean). Thus, shield top portion 432 prevents the debris from being disposed between film 206 and lens 108.

Furthermore, debris that falls or flows off the rear of shield top portion 432 flows in direction 552. Debris that flows along direction 552 flows into one or more surfaces or gutters of goggle frame 106. Certain examples of shield top portion 432 also overlap the rear of a top ledge of goggle frame 106. Such overlap may prevent debris from flowing in between goggle frame 106 and mud shield 430, further preventing or minimizing debris from flowing or being disposed in an area of goggle 400 that may affect the vision of the user or operation of various systems of goggle 400.

Figure 6A:
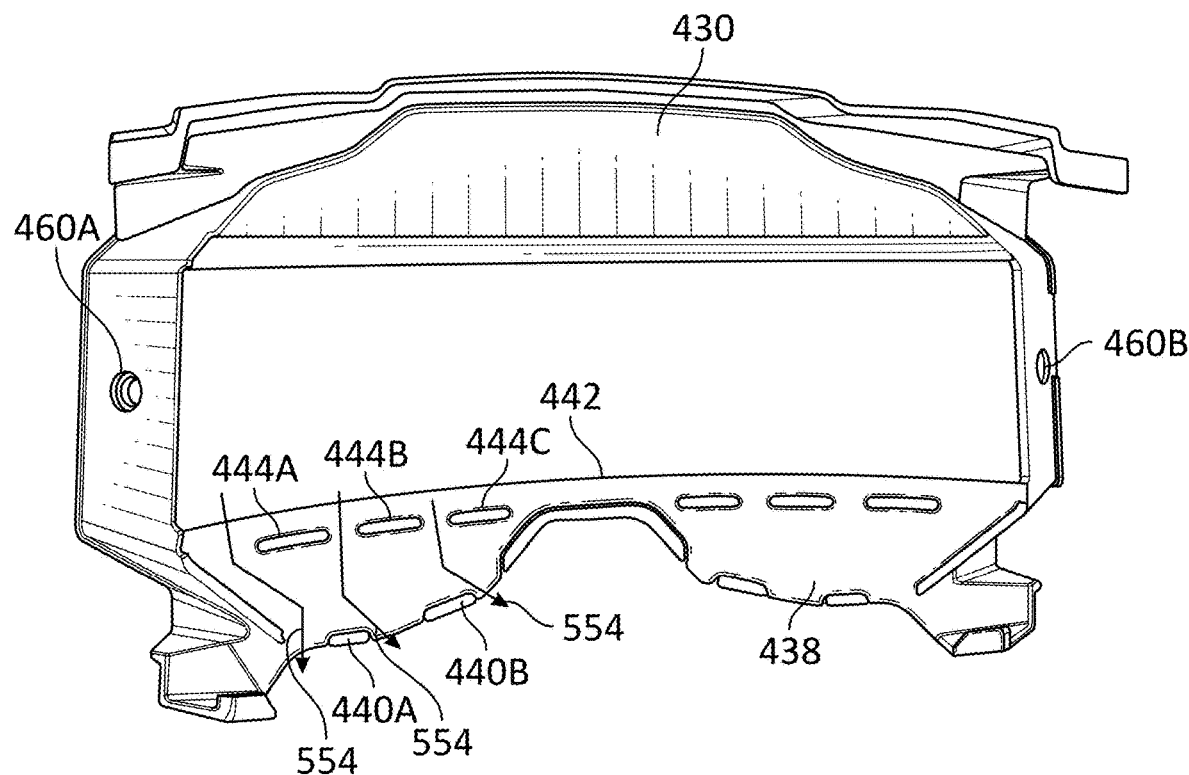
FIG. 6A is a rear view of the mud shield of FIG. 4A.
Figure 6B:
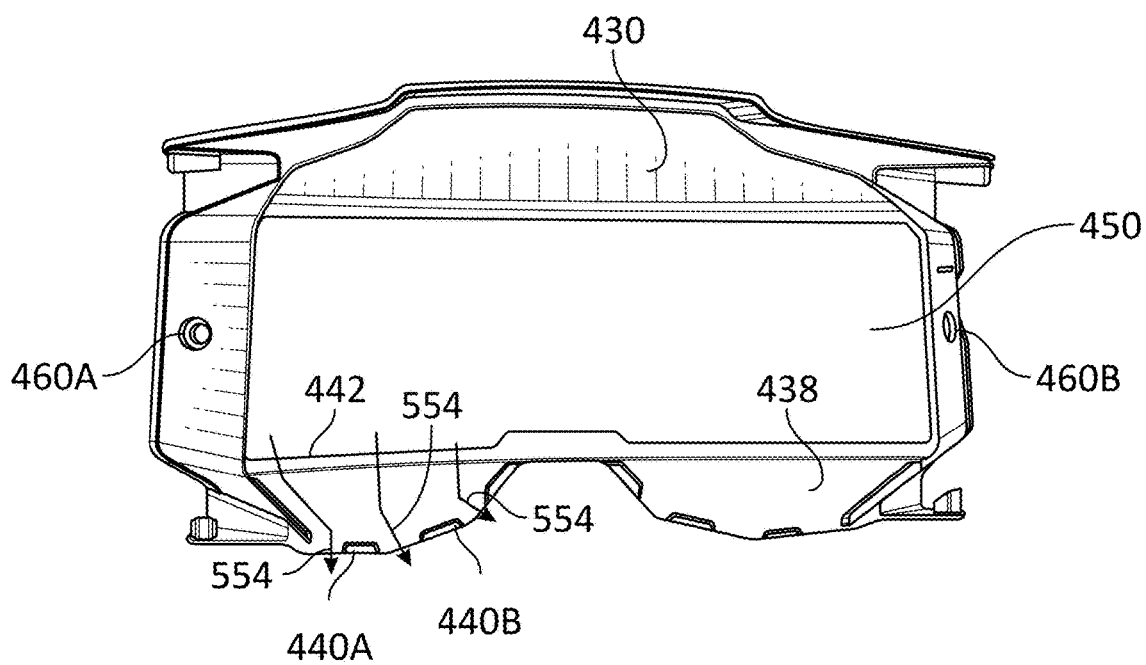
FIG. 6B is a rear view of the mud shield of FIG. 4B.

FIGS. 6A and 6B further illustrate the flow of debris within mud shield 430. FIG. 6A shows a rear view of mud shield 430 of FIG. 4A. FIG. 6B shows a rear view of mud shield 430 of FIG. 4B. As shown in FIGS. 6A and 6B, shield bottom portion 438 includes a bottom seal edge 442. In certain examples, bottom seal edge 442 is configured to contact a portion of film 206. Such examples may, thus, form a seal between the bottom of film 206 and shield bottom portion 438 to minimize debris flowing behind bottom portion 438 and apply a pressure on film 206 to aid in adhering film 206 to lens 108. Debris may then accordingly flow downward over the front of bottom portion 438 of mud shield 430.

In some examples, a gap exists between bottom seal edge 442 and film 206. Debris may then accordingly flow along direction 554 through the inside of bottom portion 438 between film 206 and lens 108 and out the bottom of bottom portion 438. Certain examples may include forms or protrusions 444A, 444B, 444C and/or 440A and 440B. For example, FIG. 6A shows mud shield 430 with forms 444A-C and 440A-B. FIG. 6B shows mud shield 430 with forms 440A-B only. Such forms 444A-C and 440A and 440B function as stand-offs to space bottom portion 438 from film 206, lens 108, goggle frame 106, or another portion of the bottom to allow debris to flow along direction 554 through the back side of mud shield 430. In some examples, these stand-off features are absent, enabling a face to face fit of the lower shield portion on the goggle lens.

When present, forms 440A and 440B and/or forms 444A-C may form a partial wind blocker on the bottom of mud shield 430. Blocking the wind prevents wind from blowing upward through the bottom of mud shield 430. Upward wind from the bottom of mud shield 430 may otherwise cause debris (e.g., dust) to also blow upward, possibly depositing the debris between film 206 and lens 108, and potentially dislodging the film from the lens. As shown in FIG. 6A, the position of forms 440A and 440B are offset from the position of forms 444A-C, causing any upward wind to change direction within the bottom portion 438, thus, increasing resistance to upward blowing wind.

As further shown in FIGS. 6A and 6B, mud shield 430 may include openings 460A and 460B. Openings 460A and 460B are configured to receive one or more pins (e.g., pins 230, 232 of canisters 202, 204). Openings 460A and 460B allow for pins 230, 232 to protrude through mud shield 430. Such pins 230, 232 that protrude through openings 460A and 460B facilitate the attachment of additional accessories, such as tear-offs, over mud shield 430. Alternatively, or additionally, mud shield 430 may include pins formed on mud shield 430 itself to allow for attachment of tear-offs.

Figure 7A:
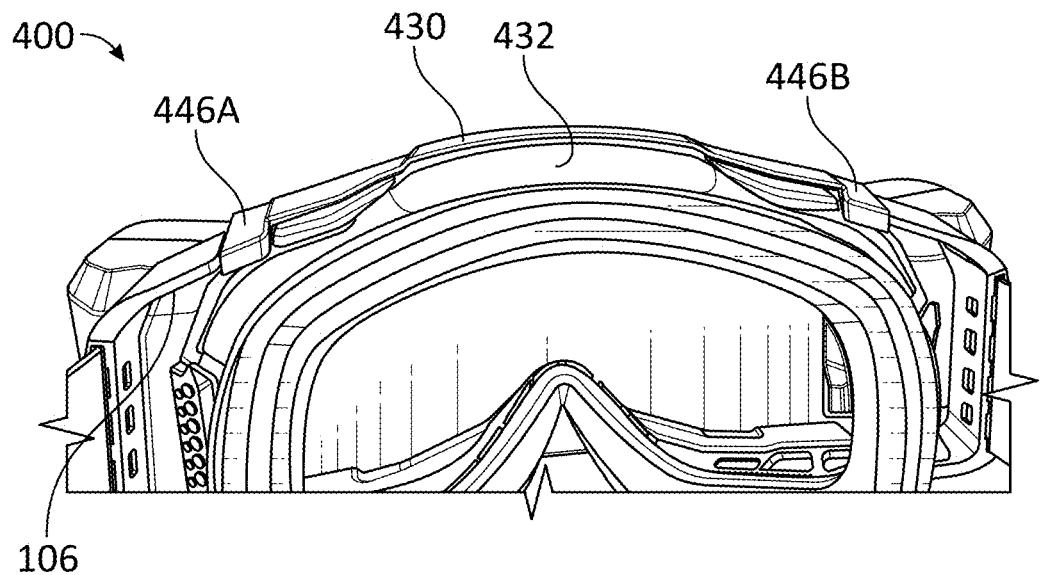
FIG. 7A is a perspective rear view of a portion of the goggle with the installed mud shield of FIG. 4A.
Figure 7B:
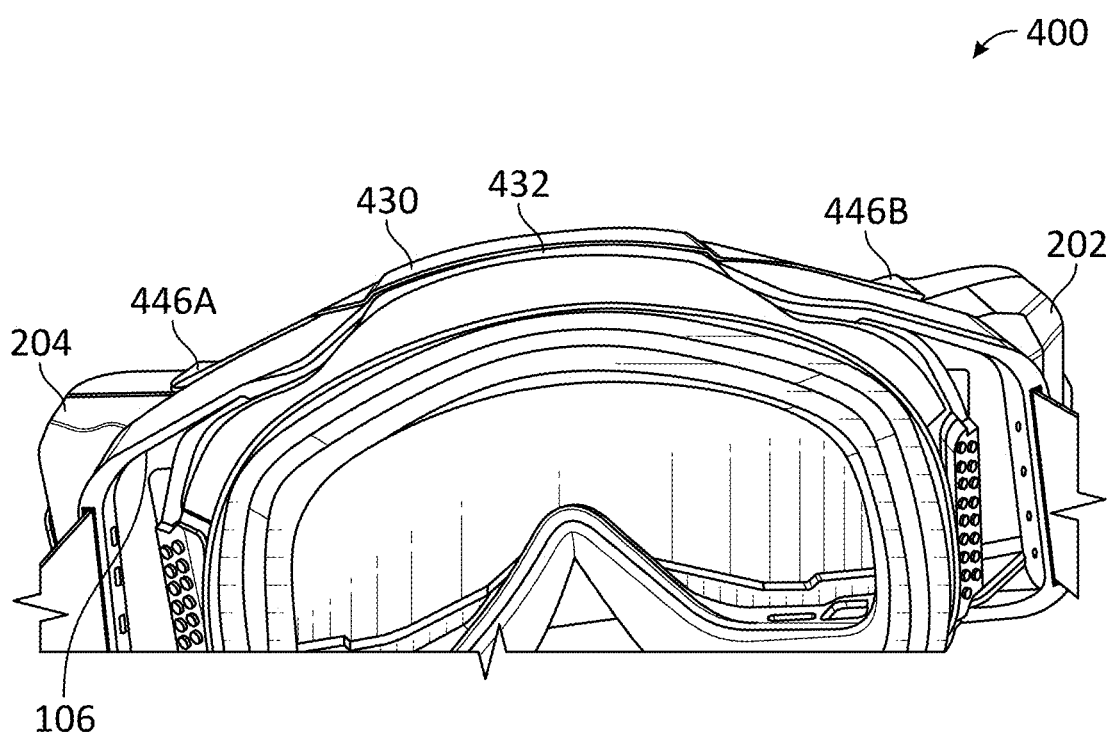
FIG. 7B is a perspective rear view of a portion of the goggle with the installed mud shield of FIG. 4B.
Figure 8A:
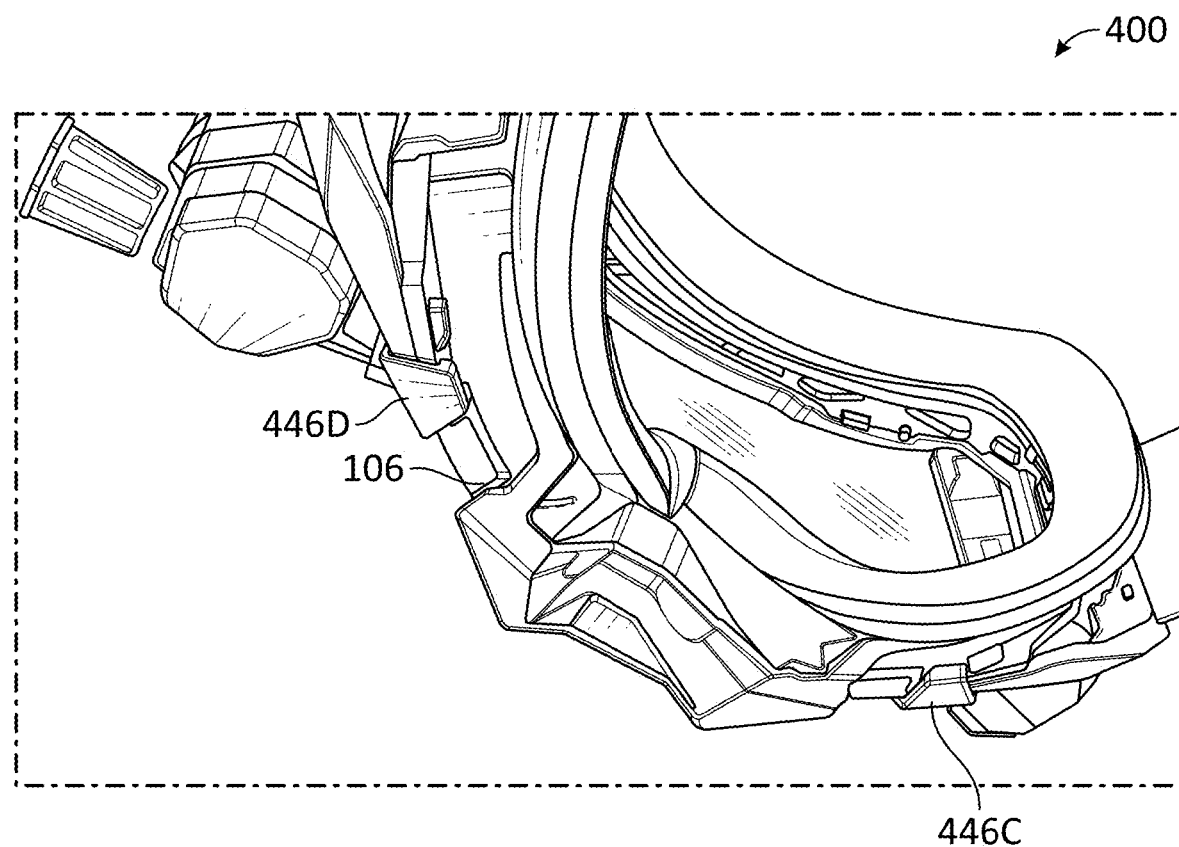
FIG. 8A is a perspective bottom view of a portion of the goggle with the installed mud shield of FIG. 4A.
Figure 8B:
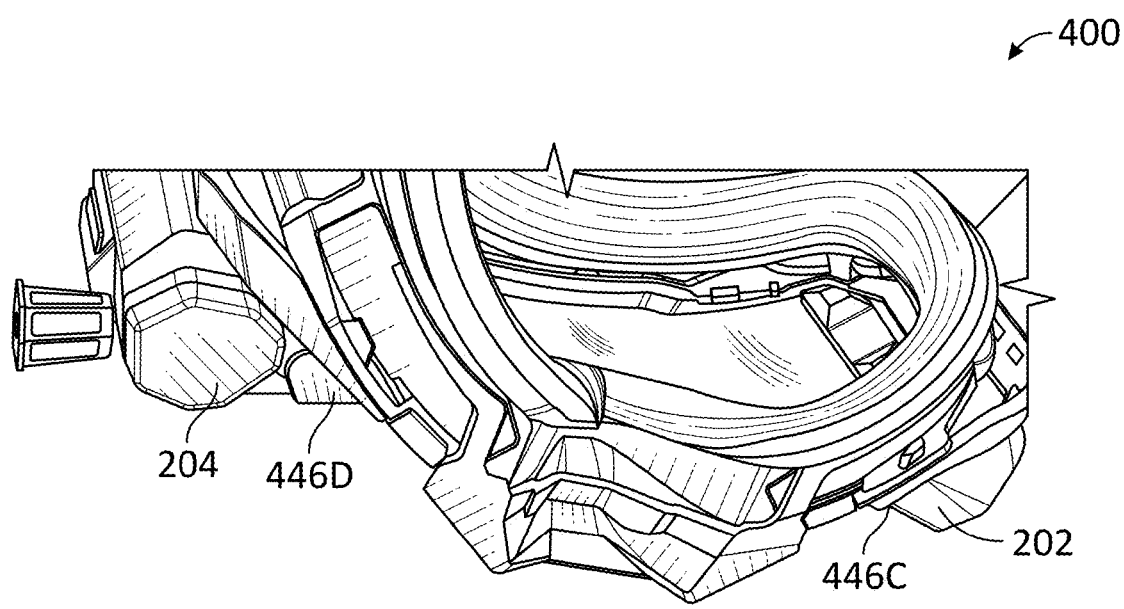
FIG. 8B is a perspective bottom view of a portion of the goggle with the installed mud shield of FIG. 4B.

FIG. 7A is a perspective rear view of a portion of goggle 400 with the installed mud shield 430 of FIG. 4A. FIG. 7B is a perspective rear view of a portion of goggle 400 with the installed mud shield 430 of FIG. 4B. FIG. 8A is a perspective bottom view of a portion of goggle 400 with the installed mud shield 430 of FIG. 4A. FIG. 8B is a perspective bottom view of a portion of goggle 400 with the installed mud shield 430 of FIG. 4B. FIGS. 7A-8B illustrate tabs 446A, 446B, 446C, and 446D of mud shield 430. Tabs 446A-D may be configured to clip over portions of goggle frame 106 and/or roll-off system 102. For example, tabs 446A-B may extend or clip over portions of goggle frame 106 (see FIG. 7A) and/or may extend or clip over portions of roll-off system 102, such as film receiving canister 204 and film dispensing canister 202, respectively (see FIG. 7B). Tabs 446C-D may extend or clip over portions of goggle frame 106 (see FIG. 8A) and/or may extend or clip over portions of roll-off system 102, such as film dispensing canister 202 and film receiving canister 204, respectively (see FIG. 8B). In certain examples, tabs 446A-D are disposed on peripheral portions of mud shield 430 (e.g., top or bottom edges and/or near or on the farthest left or right portions of mud shield 430). In certain examples, the rear portion of shield top portion 432 may be configured to contact a portion of goggle frame 106 to further prevent debris from entering into the space between mud shield 430 and goggle frame 106 and/or goggle lens 108. More or fewer tabs may be present.

Figure 9A:
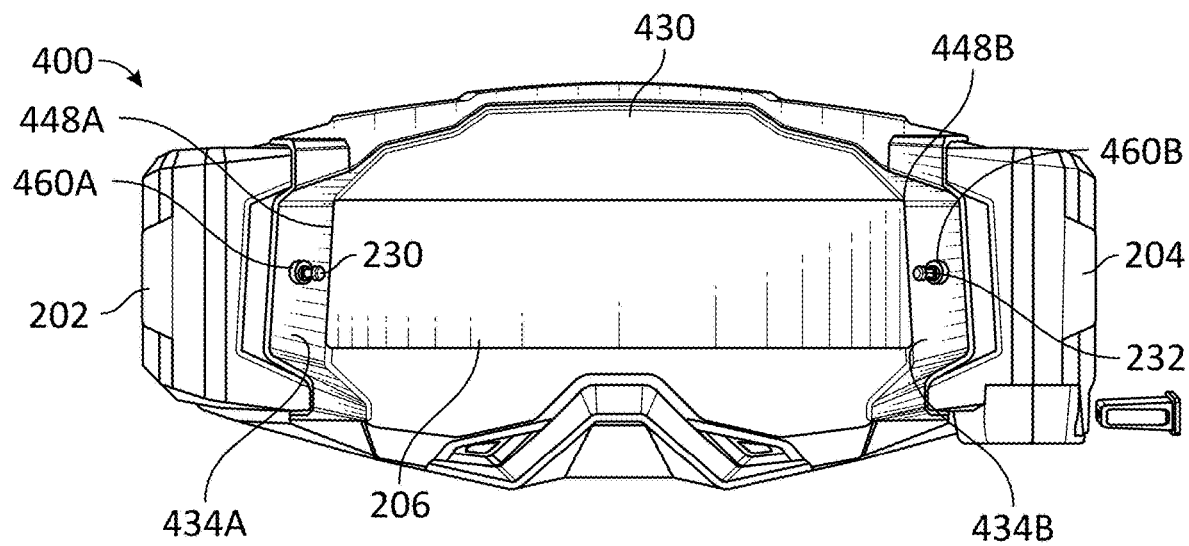
FIG. 9A is a front view of the goggle with the installed mud shield of FIG. 4A.
Figure 9B:
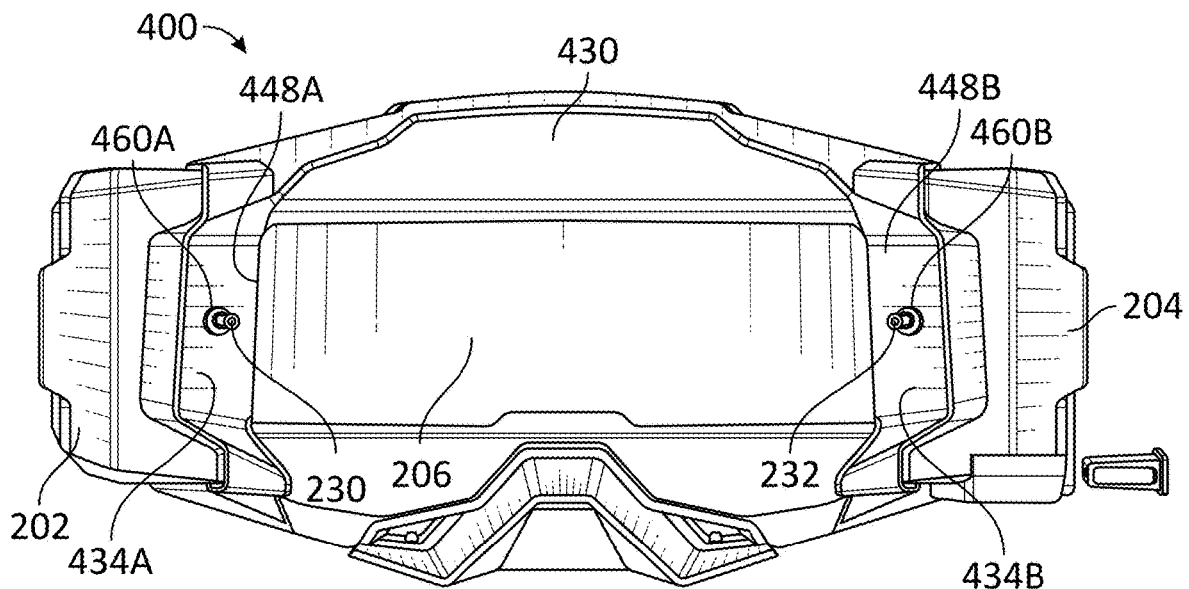
FIG. 9B is a front view of the goggle with the installed mud shield of FIG. 4B.

FIG. 9A is a front view of goggle 400 with the installed mud shield 430 of FIG. 4A. FIG. 9B is a front view of goggle 400 with the installed mud shield 430 of FIG. 4B. In FIGS. 9A and 9B, right portion 434A and left portion 434B are disposed over portions of film 206, lens 108, and/or canisters 202. Right portion 434A and left portion 434B may overlap at least a portion of canisters 202, as viewed from the front. Such overlap may direct wind over the edges of canisters 202 and away from where film 206 enters canister 202, preventing or minimizing any debris from entering canister 202.

One or both of right portion 434A and left portion 434B may include a right seal edge 448A and a left seal edge 448B, respectively. In certain examples, at least a portion of right seal edge 448A and/or left seal edge 448B are disposed over a portion of film 206. Right seal edge 448A and/or left seal edge 448B may contact film 206 so that, when film 206 is being conveyed across the surface of lens 108, right seal edge 448A and/or left seal edge 448B may wipe off film 206 before it enters one of canisters 202, 204. Such wiping action may prevent buildup of mud and/or other debris within canisters 202, 204.

C. Illustrative Method

Figure 10:
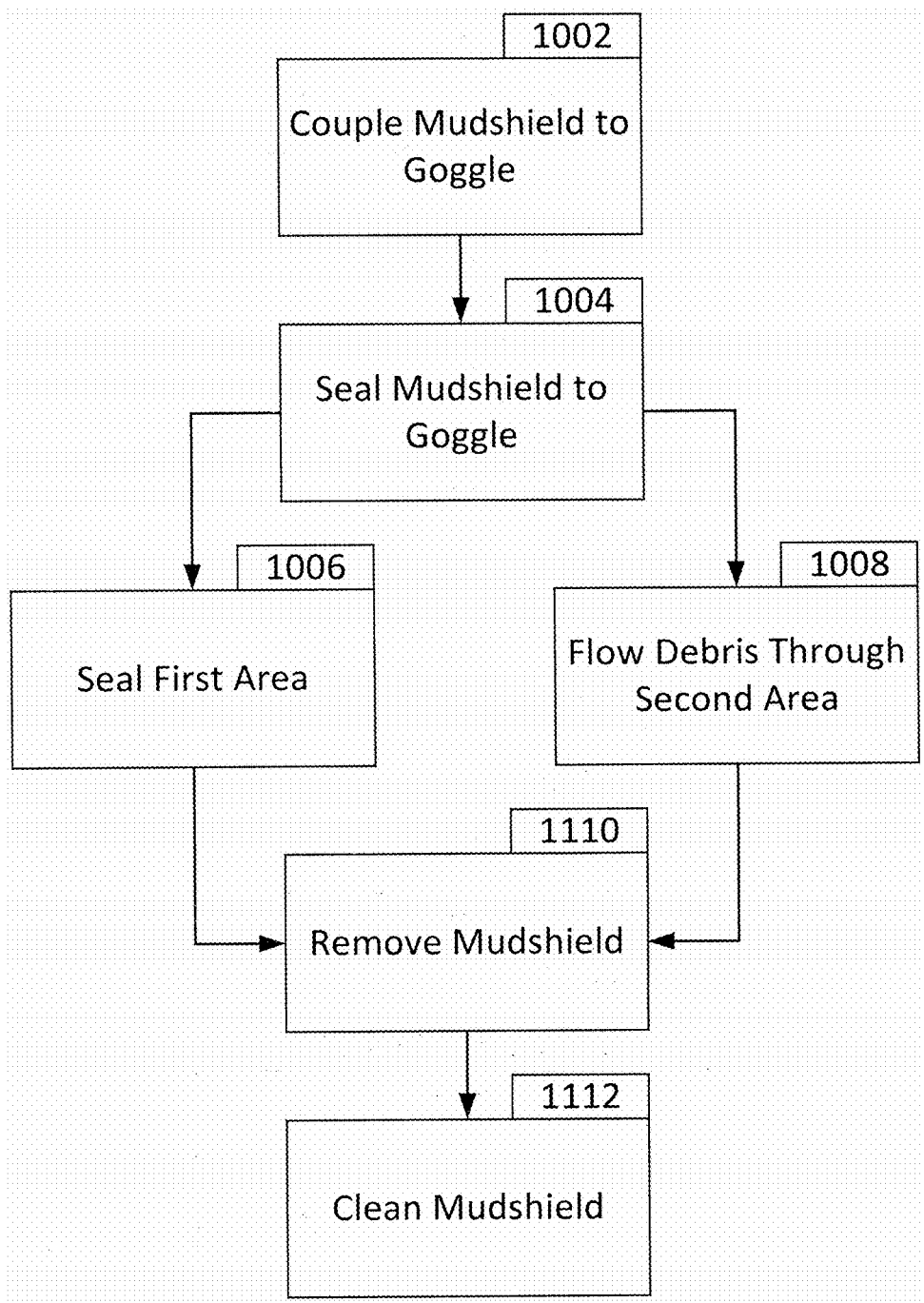
FIG. 10 is a flowchart depicting steps of an illustrative method for using a mud shield of the present disclosure.

This section describes steps of an illustrative method 1000 for using mud shield 430; see FIG. 10. Aspects of mud shields described in sections above and below may be utilized in the method steps described in this section. Where appropriate, reference may be made to components and systems that may be used in carrying out each step. These references are for illustration, and are not intended to limit the possible ways of carrying out any particular step of the method.

FIG. 10 is a flowchart illustrating steps performed in an illustrative method, and may not recite the complete process or all steps of the method. Although various steps of method 1000 are described below and depicted in FIG. 10, the steps need not necessarily all be performed, and in some cases may be performed simultaneously or in a different order than the order shown.

Mud shield 430 is referenced in the steps below. However, any mud shield disclosed herein may be utilized.

In block 1002, mud shield 430 is coupled to goggle 100 or 400 (e.g., coupled to goggle frame 106). Mud shield 430 may be secured to the goggle frame 106 via one or more tabs 446A-D. Tabs 446A-D may be disposed over a portion of goggle frame 106 and/or over portions of roll-off system 102 (e.g., film dispensing canister 202 and/or film receiving canister 204) to prevent mud shield 430 from detaching from goggle 400 unless a certain force is experienced by mud shield 430.

In block 1004, portions of mud shield 430 are sealed against portions of goggle 400. In certain examples, when mud shield 430 is coupled to goggle frame 106 and/or roll-off system 102, mud shield 430 is automatically sealed against goggle 400 or portions thereof. Alternatively, or additionally, a user may apply force to portions of mud shield 430 to seal mud shield 430 against goggle 400. Goggle 400 equipped with mud shield 430 may be worn and used.

During use of mud shield 430 equipped goggle 400, a first area or a plurality of areas may be sealed, in block 1006. Thus, debris may be prevented or minimized from entering such areas through one or more features of mud shield 430 described herein. Additionally, debris may be flowed through a second area or a plurality of areas, in block 1008. Debris may be flowed through such areas and away from mud shield 430 and/or goggle 400.

In block 1110, after mud shield 430 has been used, mud shield 430 may be removed from goggle frame 106. Mud shield 430 may then be cleaned, in block 1112.

D. Third Illustrative Mud Shield

Figure 11:
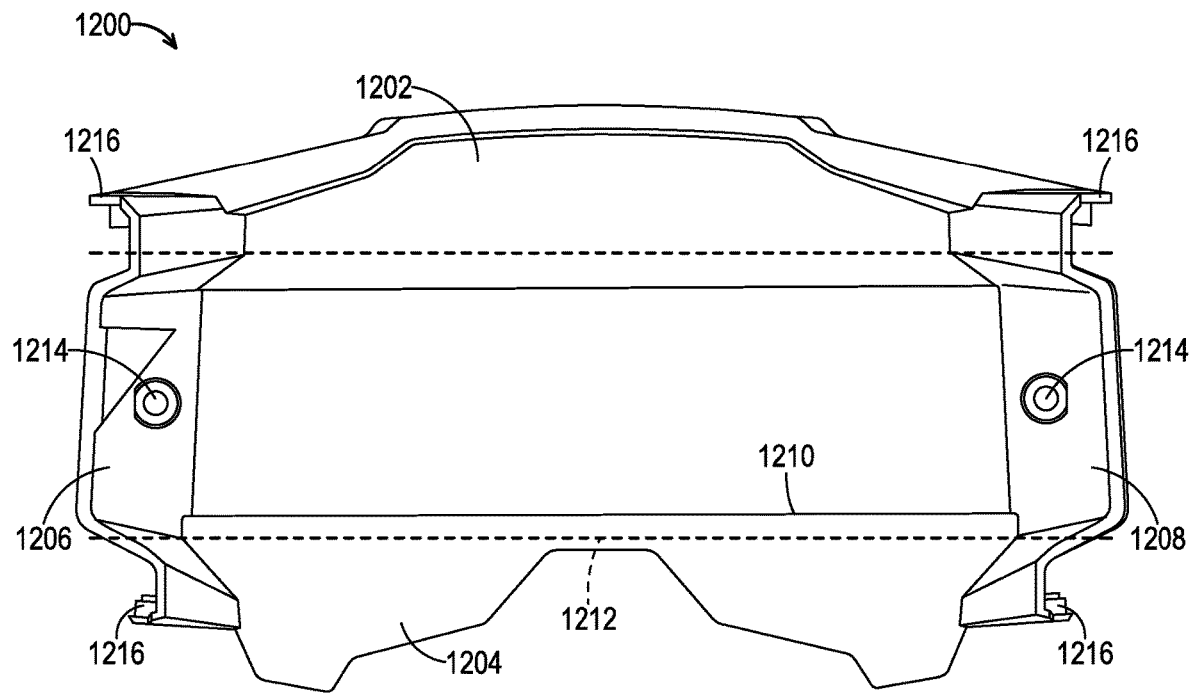
FIG. 11 is a front view of a third illustrative mud shield, in accordance with aspects of the present disclosure.
Figure 12:
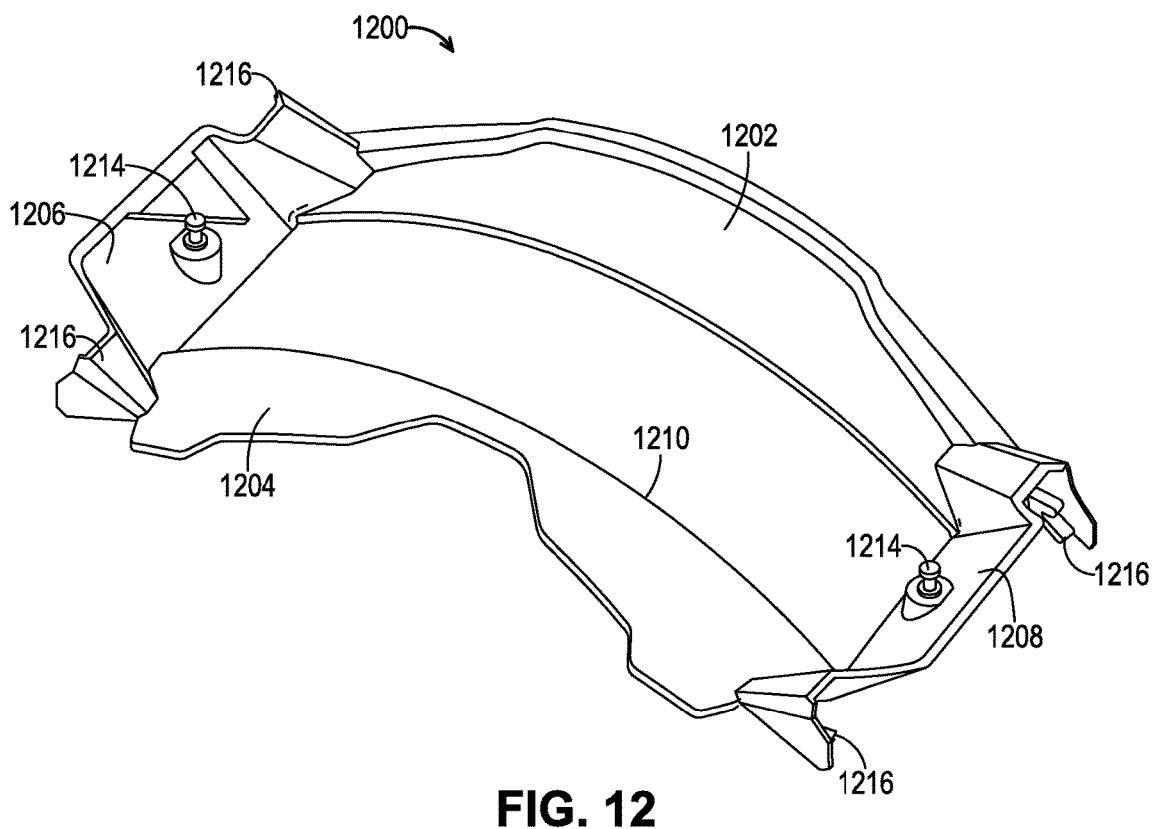
FIG. 12 is an isometric front view of the mud shield of FIG. 11.
Figure 13:
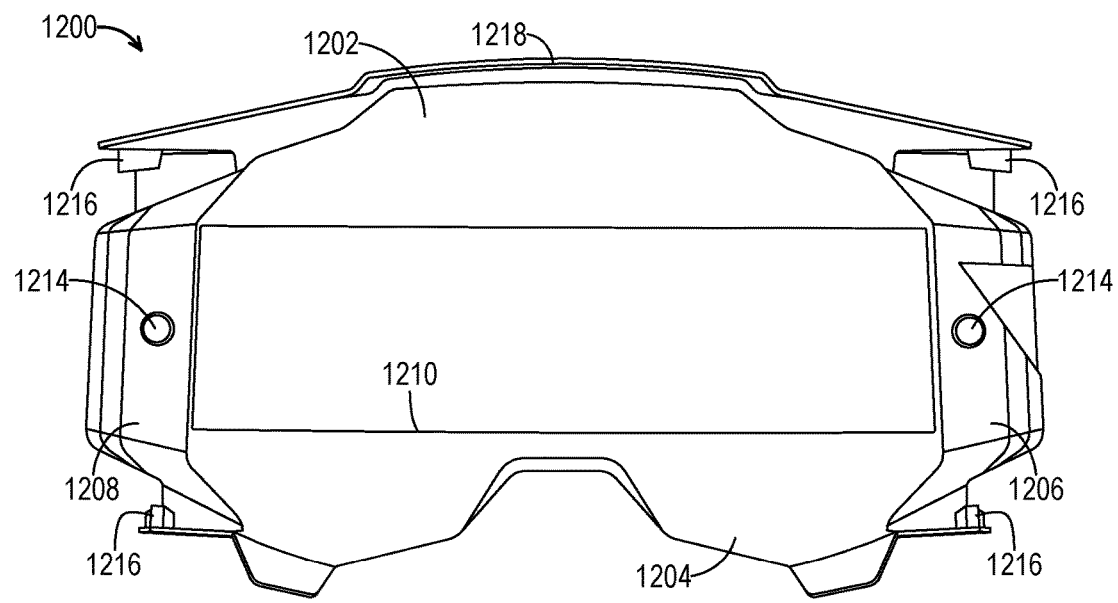
FIG. 13 is a rear view of the mud shield of FIG. 11.
Figure 14:
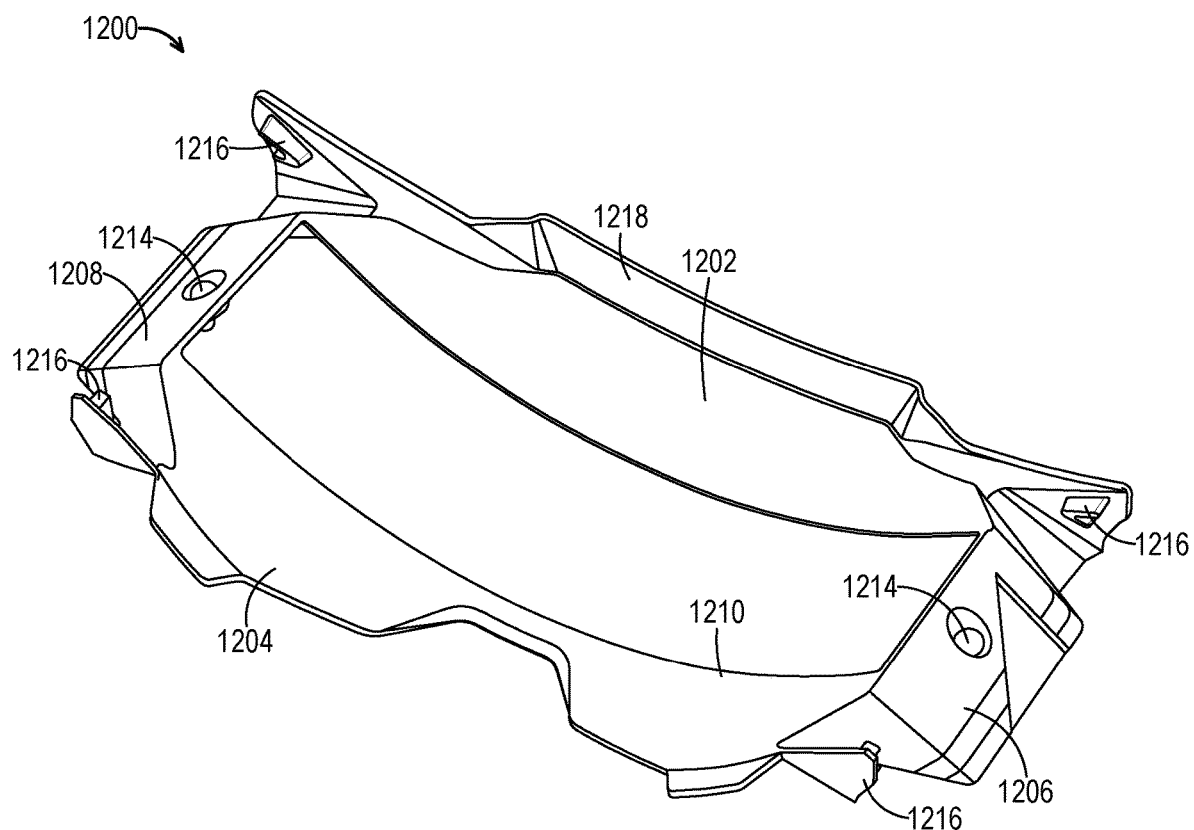
FIG. 14 is an isometric rear view of the mud shield of FIG. 11.

As shown in FIGS. 11-14, this section describes another illustrative mud shield 1200. This mud shield is an example of the mud shields described in the Overview above. FIGS. 11 and 12 depict different views of an outward-facing (or exposed to the environment) side of mud shield 1200. FIGS. 13 and 14 depict different views of an inward-facing (or user's face) side of the mud shield.

Mud shield 1200 includes an upper portion 1202 configured to mate with a top portion of goggle 100 (e.g., frame 106 and/or roll-off film system 102), a lower portion 1204 configured to mate with a bottom portion of the goggle, side portions 1206 and 1208, and a gap or viewing window 1210 formed by inner edges of portions 1202, 1204, 1206, and 1208. In this example, mud shield 1200 is transparent or translucent with respect to visible light, although in some examples, some or all of the mud shield may be opaque.

In general, mud shield 1200 is configured to conform to underlying portions of the goggle. For example, upper portion 1202 and lower portion 1204 have a curved, generally cylindrical shape where they contact the lens, and the top of upper portion 1202 is configured to fit over an upper brow ridge portion of the goggle. Lower portion 1204 has a similar overall curve, and a bottom profile configured to follow that of the lens. As shown in FIGS. 11-14, the bottom profile of the mud shield is configured to remain on the outward-facing side of the goggle and lens, and does not pass under the goggle or lens so as to avoid trapping water or debris.

Side portions 1206, 1208 are oriented transverse to the general plane of the upper and lower portions, sloping forward to conform to underlying canisters of the film roll-off system.

Window 1210 is an empty space formed in the mud shield and configured to expose an underlying portion of the lens. As shown in FIG. 11, the window is sized in a vertical dimension to overlap a film 1212 and seal the film at the top and bottom edges of the window.

Pins 1214 are integrated into sides of mud shield 1200, and are configured to removably retain one or more tear-offs typically utilized in, e.g., the motocross industry. In some examples, pins 1214 are manufactured separately from the mud shield and attached to the mud shield to form a single unit including the mud shield and pins.

Mud shield 1200 is configured to clip onto the goggle in a "four-corners" manner, with top and bottom tabs 1216 configured to mate with corresponding receptacles at back sides of the canisters of the film roll-off system.

In the depicted example, a surface 1218 projects rearward from an upper portion of shield top portion 1202, such that the surface is configured to at least partially overlap a top side of a goggle to which mud shield 1200 is mounted. Surface 1218 may tend to guide debris rearward, inhibiting debris from flowing in between the goggle and the mud shield.

E. Illustrative Combinations and Additional Examples

This section describes additional aspects and features of mud shields and related systems and methods, presented without limitation as a series of paragraphs, some or all of which may be alphanumerically designated for clarity and efficiency. Each of these paragraphs can be combined with one or more other paragraphs, and/or with disclosure from elsewhere in this application, including the materials incorporated by reference in the Cross-References, in any suitable manner. Some of the paragraphs below expressly refer to and further limit other paragraphs, providing without limitation examples of some of the suitable combinations.

A0. A mud shield including: a shield body configured to be disposed over at least a portion of a goggle, wherein the shield body comprises: a shield top portion configured to be disposed over an upper portion of the goggle and comprising a top edge; a shield bottom portion configured to be disposed over a lower portion of the goggle and comprising a bottom edge; and an opening defined, at least in part, by the top edge and the bottom edge, wherein the top edge is configured to be disposed over a film area of a lens of the goggle.

A1. The mud shield of A0, wherein the top edge comprises a top seal edge configured to contact a top portion of a film of the lens.

A2. The mud shield of A0 or A1, wherein the shield top portion is configured to fully cover a top portion of the lens of the goggle above the film area.

A3. The mud shield of any one of paragraphs A0 through A2, wherein the bottom edge comprises a bottom seal edge configured to a contact a bottom portion of a film of the lens.

A4. The mud shield of any one of paragraphs A0 through A3, further comprising: a left portion comprising a left edge; and a right portion comprising a right edge, wherein the opening is rectangular in shape and is further defined, at least in part, by the left edge and the right edge.

A5. The mud shield of A4, wherein the left edge comprises a left seal edge, wherein the right edge comprises a right seal edge, and wherein at least portions of the left seal edge and the right seal edge are configured to be disposed on the film.

A6. The mud shield of A4, wherein the left portion and the right portion are configured to cover at least a portion of a left canister and a right canister, respectively.

A7. The mud shield of any one of paragraphs A0 through A6, wherein the shield bottom portion comprises one or more forms on a rear side of the shield bottom portion.

A8. The mud shield of A7, wherein the forms are configured to dispose at least a portion of the bottom edge away from the film.

A9. The mud shield of any one of paragraphs A0 through A8, further comprising a tab configured couple the shield body to the goggle.

A10. The mud shield of any one of paragraphs A0 through A9, further comprising a pin opening configured to allow a pin of the goggle or a canister to pass through.

B0. A method of using the mud shield of any one of paragraphs A0 through A10, the method comprising: coupling the mud shield to the goggle; and preventing or minimizing debris from flowing into the upper portion of the goggle with the shield top portion.

C0. A goggle system including: a goggle comprising: a goggle frame; and a lens coupled to the goggle frame and comprising a film area configured to receive a film; and a mud shield comprising: a shield body configured to be disposed over at least a portion of the goggle, wherein the shield body comprises: a shield top portion configured to be disposed over an upper portion of the goggle and comprising a top edge; a shield bottom portion configured to be disposed over a lower portion of the goggle and comprising a bottom edge; and an opening defined, at least in part, by the top edge and the bottom edge, wherein the top edge is configured to be disposed over the film area.

C1. The goggle system of C0, further comprising the film, wherein the film is conveyed across the lens.

C2. The goggle system of C1, wherein the top edge comprises a top seal edge configured to contact a top portion of the film.

C3. The goggle system of C1, further comprising a left canister and a right canister, wherein the film is conveyed from one of the left canister or the right canister to the other of the left canister or the right canister.

C4. The goggle system of any one of paragraphs C0 through C3, wherein the shield top portion is configured to fully cover a top portion of the lens of the goggle above the film area.

C5. The goggle system of any one of paragraphs C0 through C4, wherein the bottom edge comprises a bottom seal edge configured to a contact a bottom portion of the film.

C6. The goggle system of any one of paragraphs C0 through C5, wherein the mud shield further comprises: a left portion comprising a left edge; and a right portion comprising a right edge, wherein the opening is rectangular in shape and is further defined, at least in part, by the left edge and the right edge.

C7. The goggle system of C6, wherein the left edge comprises a left seal edge, wherein the right edge comprises a right seal edge, and wherein at least portions of the left seal edge and the right seal edge are configured to be disposed on the film.

Advantages, Features, and Benefits

The different embodiments and examples of the mud shield systems and methods described herein provide several advantages over known solutions. For example, illustrative embodiments and examples described herein allow a mud shield to be selectively attached to a goggle, enabling a user to replace the mud shield as desired without replacing the entire goggle.

Additionally, and among other benefits, illustrative embodiments and examples described herein allow one or more tear-offs and a conveyable film to protect a goggle lens by receiving dirt and/or other vision-obscuring debris that would otherwise accumulate on the lens. This increases the amount of time a user of the goggle can wear the goggle (e.g., during a motocross or other event) before it becomes difficult or impossible to see through the lens.

No known system or device can perform these functions. However, not all embodiments and examples described herein provide the same advantages or the same degree of advantage.

CONCLUSION

The disclosure set forth above may encompass multiple distinct examples with independent utility. Although each of these has been disclosed in its preferred form(s), the specific embodiments thereof as disclosed and illustrated herein are not to be considered in a limiting sense, because numerous variations are possible. To the extent that section headings are used within this disclosure, such headings are for organizational purposes only. The subject matter of the disclosure includes all novel and nonobvious combinations and subcombinations of the various elements, features, functions, and/or properties disclosed herein. The following claims particularly point out certain combinations and subcombinations regarded as novel and nonobvious. Other combinations and subcombinations of features, functions, elements, and/or properties may be claimed in applications claiming priority from this or a related application. Such claims, whether broader, narrower, equal, or different in scope to the original claims, also are regarded as included within the subject matter of the present disclosure.

The invention claimed is:

1. A mud shield for a goggle, the mud shield comprising:
a shield body configured to be disposed over at least a portion of a goggle, the shield body having a three-dimensional shape conforming to a shape of the goggle, wherein the shield body includes:
a shield top portion configured to be disposed over an outward-facing upper portion of the goggle, an upper periphery of the shield top portion projecting rearward and configured to at least partially overlap a top side of the goggle, and a lower periphery of the shield top portion defining a first edge; and
a shield bottom portion configured to be disposed over a lower portion of the goggle, an upper periphery of the shield bottom portion defining a second edge, and a lower periphery of the shield bottom portion defining a lower periphery of the shield body, wherein the lower periphery of the shield body has a bottom profile configured to follow a corresponding bottom profile of the goggle, and an entirety of the bottom profile of the lower periphery of the shield body is configured to be disposed on an outward-facing side of the goggle without extending rearward;
wherein an opening extends between the first edge and the second edge, the opening defining a viewing window and being configured to expose an underlying portion of the goggle when installed; and
wherein the first edge of the shield top portion comprises a first sealing surface configured to contact a top portion of a film dispensed across a film area of a lens of the goggle.

2. The mud shield of claim 1, wherein the second edge comprises a second sealing surface configured to a contact a bottom portion of the film.

3. The mud shield of claim 1, wherein the shield top portion is configured to fully cover a top portion of the lens of the goggle.

4. The mud shield of claim 1, wherein the mud shield includes one or more tabs configured to removably clip the shield body to a frame of the goggle.

5. The mud shield of claim 1, further comprising:
a left portion defining a left edge of the opening; and
a right portion defining a right edge of the opening;
wherein the opening is rectangular or trapezoidal in shape.

6. The mud shield of claim 5, wherein the left edge comprises a left sealing surface and the right edge comprises a right sealing surface, and at least portions of the left and right sealing surfaces are configured to contact the film dispensed across the film area of the lens of the goggle.

7. The mud shield of claim 5, wherein the left portion and the right portion are further configured to cover at least a portion of a left canister and a right canister of a roll-off film dispensing system of the goggle.

8. The mud shield of claim 1, further comprising one or more mounting pins extending from a front surface of the mud shield.

9. The mud shield of claim 1, wherein the shield top portion and the shield bottom portion are formed together as a single piece.

10. A goggle system comprising:
a goggle including a goggle frame and a lens coupled to the goggle frame;

a film selectively conveyable across the lens; and a mud shield including a shield body coupled to the goggle, the shield body having a three-dimensional shape conforming to a shape of the goggle;

wherein the shield body comprises:

a shield top portion disposed over an outward-facing upper portion of the goggle and having a lower periphery defining a first edge, and an upper periphery projecting rearward and configured to at least partially overlap a top side of the goggle;

a shield bottom portion disposed over a lower portion of the goggle and having a lower periphery defining a lower periphery of the shield body, wherein the lower periphery of the shield body has a bottom profile configured to follow a corresponding bottom profile of the goggle, wherein an entirety of the bottom profile of the lower periphery of the shield body is configured to be disposed on an outward-facing side of the goggle without extending rearward, and an upper periphery of the shield bottom portion defines a second edge; and an opening defined, at least in part, by the first and second edges;

wherein the shield top portion and the shield bottom portion are formed together as a single piece.

11. The goggle system of claim 10, wherein the first edge comprises a first seal edge configured to contact a top portion of the film.

12. The goggle system of claim 10, wherein the second edge comprises a second seal edge configured to a contact a bottom portion of the film.

13. The goggle system of claim 10, further comprising a left canister and a right canister, wherein the film is selectively conveyable from one of the left canister or the right canister to the other of the left canister or the right canister.

14. The goggle system of claim 10, wherein the shield top portion is configured to fully cover a top portion of the lens of the goggle.

15. The goggle system of claim 10, wherein the mud shield further comprises:

a left portion defining a left edge of the opening; and a right portion defining a right edge of the opening, wherein the opening is rectangular or trapezoidal in shape.

16. The goggle system of claim 15, wherein the left edge comprises a left sealing surface, the right edge comprises a right sealing surface, and at least portions of the left sealing surface and the right sealing surface are configured to contact the film dispensed across a film area of the lens.

17. The goggle system of claim 10, further comprising one or more mounting pins extending from a front surface of the mud shield.

18. The goggle of claim 10, wherein the bottom profile of the lower periphery of the shield body mirrors a bottom profile of a lower periphery of the lens.

* * * * *